United States Patent [19]

Grethe et al.

[11] 3,957,800
[45] May 18, 1976

[54] PROCESSES AND INTERMEDIATES FOR CIS OR TRANS 2- OR 3-(1-ACYL-3-VINYL-4-PIPERIDINE)ACETIC OR PROPIONIC ACID ESTERS

[75] Inventors: Güenter Grethe, North Caldwell; Milan Radoje Uskokovic, Upper Montclair, both of N.J.

[73] Assignee: Hoffmann-La Roche Inc., Nutley, N.J.

[22] Filed: May 23, 1975

[21] Appl. No.: 580,492

Related U.S. Application Data

[62] Division of Ser. No. 362,604, May 21, 1973, which is a division of Ser. No. 100,370, Dec. 21, 1970, abandoned.

[52] U.S. Cl. ............................................ 260/293.88
[51] Int. Cl.$^2$ ........................................ C07D 211/34
[58] Field of Search ............................... 260/293.88

[56] References Cited
UNITED STATES PATENTS
3,317,546   5/1967   Cislak et al. .................... 260/294

*Primary Examiner*—G. Thomas Todd
*Attorney, Agent, or Firm*—Samuel L. Welt; George M. Gould; William G. Isgro

[57] ABSTRACT

Cis or trans 2-(1-acyl-3-vinyl-4-piperidine)acetic acid esters and cis or trans 3-(1-acyl-3-vinyl-4-piperidine)propionic acid esters, antipodes and racemates thereof, are prepared, inter alia, from the corresponding cis or trans 2- or 3[1-acyl-3-(2-chloroethyl)-4-piperidine]acetic or propionic acid esters, respectively. The cis or trans 2- or 3-(1-acyl-3-vinyl-4-piperidine)acetic or propionic acid esters are useful as intermediates for the synthesis of quinine and quinidine and analogs and stereoisomers thereof.

3 Claims, No Drawings

PROCESSES AND INTERMEDIATES FOR CIS OR TRANS 2- OR 3-(1-ACYL-3-VINYL-4-PIPERIDINE)ACETIC OR PROPIONIC ACID ESTERS

CROSS-REFERENCE TO RELATED APPLICATIONS

This application is a division of U.S. patent application Ser. No. 362,604, filed May 21, 1973, which in turn is a division of Ser. No. 100,370, filed Dec. 21, 1970, now abandoned.

BRIEF SUMMARY OF THE INVENTION

In a process aspect the invention relates to the preparation of compounds of the formula

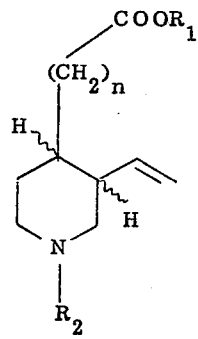

wherein $R_1$ is hydrogen or lower alkyl; $R_2$ is acyl, halo-substituted acyl, lower alkoxy substituted acyl, lower alkyl substituted acyl, and $n$ is 1 or 2, by pyrrolyzing the compound of the formula

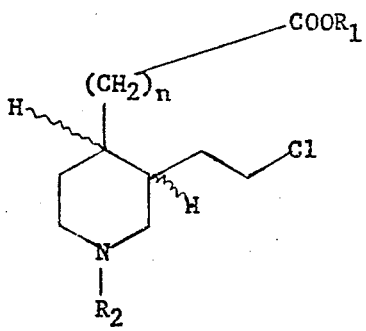

wherein $R_1$, $R_2$ and $n$ are as hereinbefore described.

In another process aspect, the invention relates to the preparation of the compounds of formula I by treating a compound of the formula

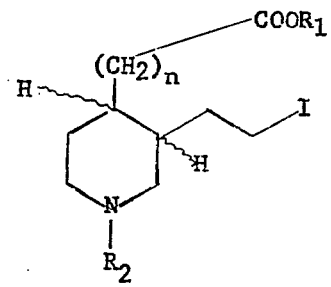

wherein $R_1$, $R_2$ and n are as hereinbefore described, with an inorganic salt in the presence of an organic base.

In a still further process aspect, the invention relates to the preparation of the compounds of formula I by treating a compound of the formula

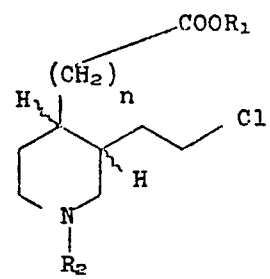

wherein $R_1$, $R_2$ and $n$ are as hereinbefore described, with an alkali metal alkoxide such as potassium-t-butoxide.

In the foregoing processes, when $R_1$ is hydrogen, if desired, the additional step of esterification can be carried out to yield the compounds of formula I wherein $R_1$ is lower alkyl.

The invention also relates to compounds of the formulas

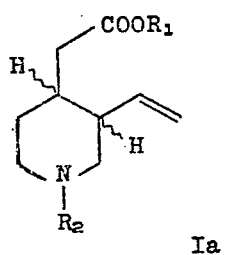

Ia

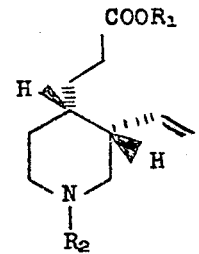

Ib ,

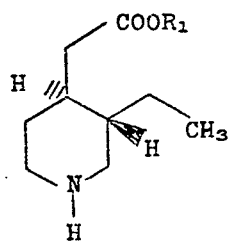

IIa ,

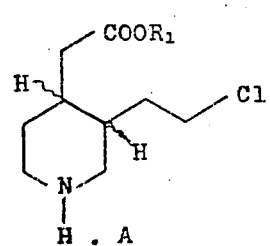

IVa ,

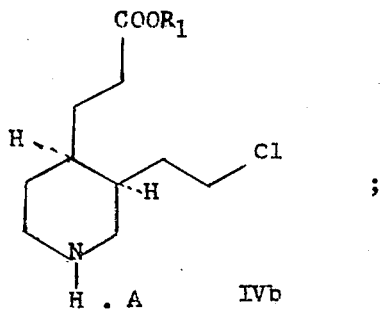

IVb

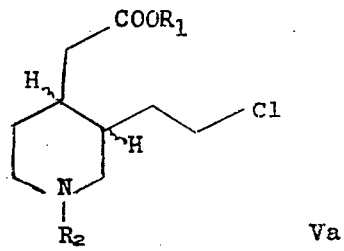

Va

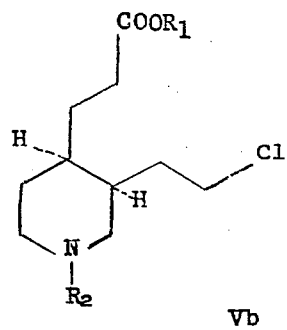

Vb ; and

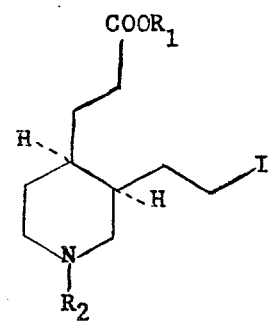

VIa wherein $R_1$ and $R_2$ are as hereinbefore described, and A is an inorganic acid such as sulfuric acid, phosphoric acid and the like, or an organic acid, for example, a lower alkanoic acid such as acetic acid, or a halogenated lower alkanoic acid such as trifluoroacetic acid, trichloroacetic acid and the like.

DETAILED DESCRIPTION OF THE INVENTION

As used herein, the term "lower alkyl" denotes a hydrocarbon of 1–7 carbon atoms, for example, methyl, ethyl, t-butyl, propyl, isopropyl, pentyl, hexyl, heptyl, and the like; preferred are methyl and ethyl. The term "lower alkoxy" denotes an alkyl ether group in which the lower alkyl group is as described above, for example, methoxy, ethoxy, propoxy, pentoxy, and the like. The term "halogen" denotes all the halogens, i.e., bromine, chlorine, fluorine and iodine; preferred are chlorine and bromine. The term "acyl" denotes an alkanoyl group derived from an aliphatic carboxylic acid of 1–7 carbon atoms, for example, formyl, acetyl, propionyl, butanoyl, and the like; and an "aroyl" group derived from an aromatic carboxylic acid such as benzoyl, phenacetyl and phthaloyl.

The preparation of the cis or trans 2- or 3-(1-acyl-3-vinyl-4-piperidine)acetic or propionic acid esters of formula I, antipodes or racemates thereof, can be carried out as set forth in Reaction Scheme I.

Reaction Scheme I

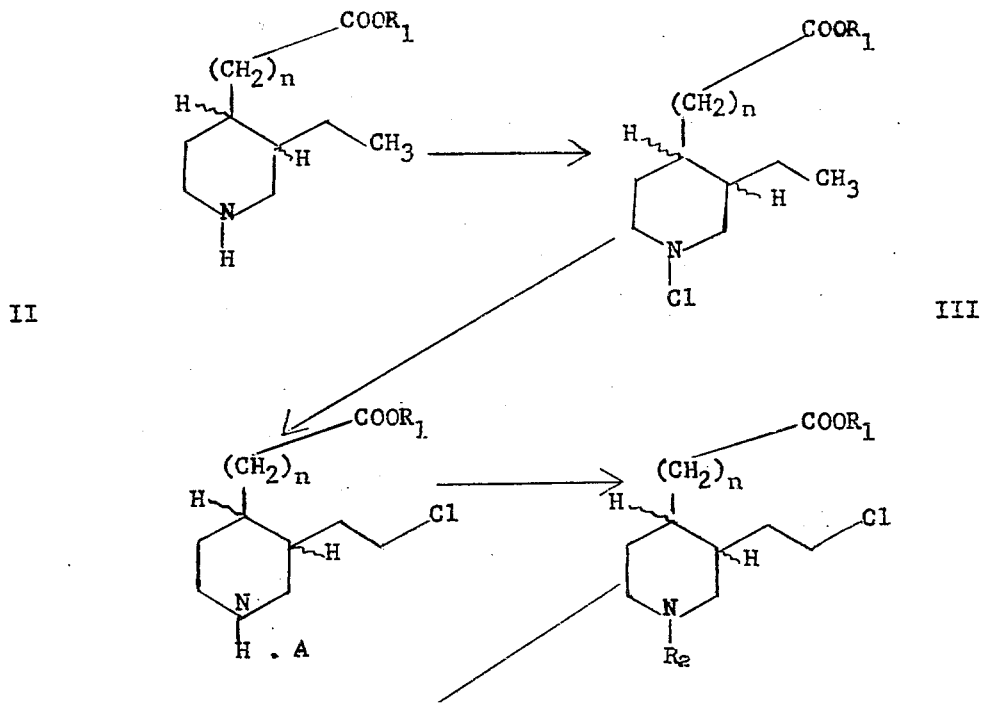

IV 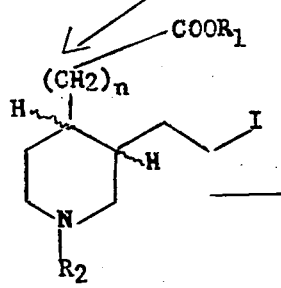 V 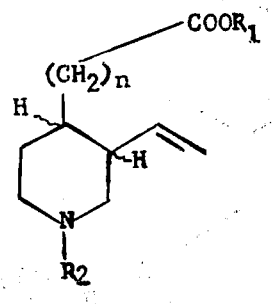

VI
                                    I wherein $R_1$, $R_2$ and $n$ are as previously described, and A is an inorganic acid such as sulfuric acid, phosphoric acid and the like, or an organic acid, for example, a lower alkanoic acid such as acetic acid, or a halogenated lower alkanoic acid such as trifluoroacetic acid, trichloroacetic acid and the like.

In Reaction Scheme I, the cis or trans 2-(3-ethyl-4-piperidine)acetic acids or esters and cis or trans 3-(3-ethyl-4-piperidine)propionic acids or esters of formula II when $n$ is 1 and 2, respectively antipodes or racemates thereof, are converted to the corresponding cis or trans 2-or 3-(1-chloro-3-ethyl-4-piperidine)acetic or propionic acids or esters of formula III, by utilizing a chlorinating agent, for example, N-chlorosuccinimide, N-chloroacetamide, alkali metal hypochlorite such as sodium hypochlorite and the like. The reaction is conducted in an inert organic solvent, for example, a hydrocarbon such as benzene, a halogenated hydrocarbon such as dichloromethane, an alkanol such as methanol, ethanol and the like, an ether such as diethylether, dioxane, tetrahydrofuran and the like. The reaction temperature is not critical; however, preferably, it is in the range of about 0°C. and about room temperature.

The conversion of the compounds of formula III, their antipodes or racemates, to the corresponding cis or trans 2-or 3-[3-(2-chloroethyl)-4-piperidine]acetic or propionic acid or ester salts of the formula IV is effected by irridiation with an ultraviolet light source such as a 200W-Hanovia high-pressure mercury lamp in an acid such as previously described or in a mixture of these acids such as acetic/sulfuric acid. The reaction temperature is not critical. However, preferably, it is in the range of about 0°C. to about room temperature.

The conversion of the compounds of formula IV, antipodes or racemates thereof, to the corresponding cis or trans 2- or 3-[1-acyl-3-(2-chloroethyl)-4-piperidine]acetic or propionic acids or esters of formula V, is effected utilizing acid chlorides, such as acetylchloride or benzoylchloride, and the like, in an inert organic solvent, for example, a hydrocarbon such as benzene, a halogenated hydrocarbon, such as dichloromethane, chloroform, and the like, or ethers such as diethyl ether, tetrahydrofuran, dioxane, and the like.

The pH of the reaction mixture is maintained between about 6 to about 10 utilizing, for example, alkali metal carbonates such as sodium or potassium carbonate. The reaction temperature is not critical; however, preferably, it is in the range of about 0°C. and about room temperature.

The conversion of the compounds of formula V, antipodes or racemates thereof, to the corresponding cis or trans 2- or 3-[1-acyl-3-(2-iodoethyl)-4-piperidine]acetic or propionic acids or esters of the formula VI, is effected utilizing an alkali metal iodide such as potassium iodide, sodium iodide, and the like, in an inert organic solvent, for example, dimethylsulfoxide, dimethylformamide, acetonitrile, alkanols such as methanol, ethanol, and the like, or ketones such as acetone, methylethylketone and the like. The temperature is not critical; however, preferably, it is in the range of about 0°C. and about the reflux temperature of the reaction mixture.

The conversion of the compounds of formula VI, antipodes or racemates thereof, to the corresponding cis or trans 2- or 3-(1-acyl-3-vinyl-4-piperidine)acetic or propionic acids or esters of the formula I, is effected utilizing an organic base, for example, pyridine, β-collidine, dimethylformamide and the like. Advantageously, an inorganic salt, for example, lithium bromide, lithium chloride, lithium carbonate, silver fluoride, silver carbonate and the like, may be utilized in the reaction. The reaction temperature is not critical; however, preferably, it is in the range of about room temperature and about the reflux temperature of the reaction mixture.

Another aspect of the invention comprises the conversion of the compounds of formula V, antipodes or racemates thereof, to the corresponding cis or trans 2- or 3-(1-acyl-3-vinyl-4-piperidine)acetic or propionic acids or esters of the formula I, by pyrrolysis, preferably at a temperature in the range of 150°C. and about 250°C. The reaction can be conducted at atmospheric pressure; however, preferably it is conducted at reduced pressure, for example, in the range of about 0.1 mm/Hg to 0.01 mm/Hg.

Still another aspect of the invention is illustrated by Reaction Scheme II which follows.

Reaction Scheme II

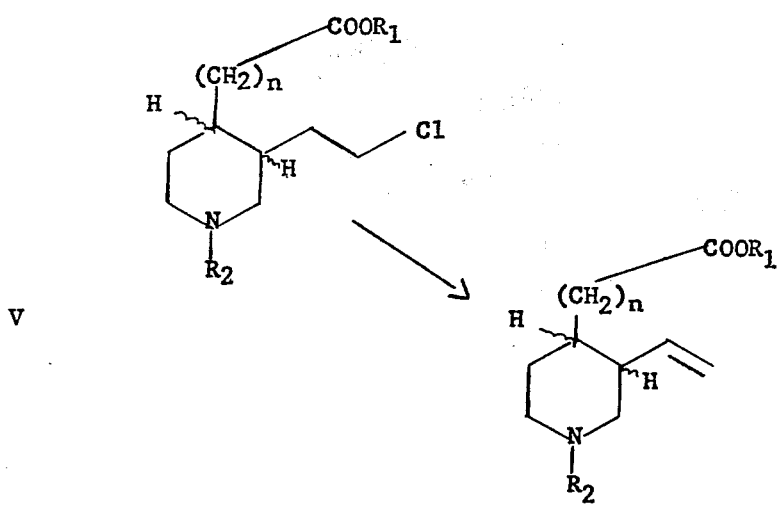

wherein $R_1$, $R_2$ and $n$ are as previously described.

In Reaction Scheme II, the cis or trans 2- or 3-[1-acyl-3-(2-chloroethyl)-4-piperidine]acetic or propionic acid esters of formula V, antipodes or racemates thereof, when $R_1$ is lower alkyl, are converted to the corresponding cis or trans 2- or 3-[1-acyl-3-(2-chloroethyl)-4-piperidine]acetic or propionic acids of formula V wherein $R_1$ is hydrogen by treatment with a base, for example, an alkali metal hydroxide, such as sodium hydroxide, potassium hydroxide or an alkaline earth hydroxide, such as calcium hydroxide and the like. Conveniently, the reaction is carried out in a solvent such as water, an alkanol, dimethylformamide and the like. The reaction temperature is not critical; however, preferably, it is in the range of about 0° to about the reflux temperature of the reaction mixture.

The conversion of the compounds of formula V when $R_1$ is hydrogen, antipodes or racemates, to the corresponding cis or trans 2- or 3-(1-acyl-3-vinyl-4-piperidine)acetic or propionic acids of formula I wherein $R_1$ is hydrogen, antipodes or racemates thereof, is effected by the treatment with an alkali metal alkoxide, such as potassium tertiary butoxide and the like, in the presence of a solvent, for example, dimethylsulfoxide, a hydrocarbon, such as benzene, and the like, an alkanol, such as methanol, ethanol, propanol, and the like. The conversion of the compounds of formula I, when $R_1$ is hydrogen, their antipodes or racemates, to the corresponding compounds of formula I when $R_1$ is lower alkyl is effected in an alkanol such as methanol, ethanol, propanol and the like in the presence of an inorganic acid such as hydrochloric hydrobromic, sulfuric acid and the like. Diazomethane may also be utilized if the ester is to be a methyl ester. The reaction temperature is not critical; however, preferably, it is in the range of about room temperature to about reflux temperature of the reaction mixture.

The cis and trans 2- or 3-(1-acyl-3-vinyl-4-piperidine) acetic and propionic acid esters, antipodes or racemates thereof, are useful as intermediates in the preparation of quinine, quinidine and analogs thereof. More particularly, the cis-3-(1-acyl-3-vinyl-4-piperidine)propionic acid esters are used as illustrated in Reaction Scheme III.

Reaction Scheme III

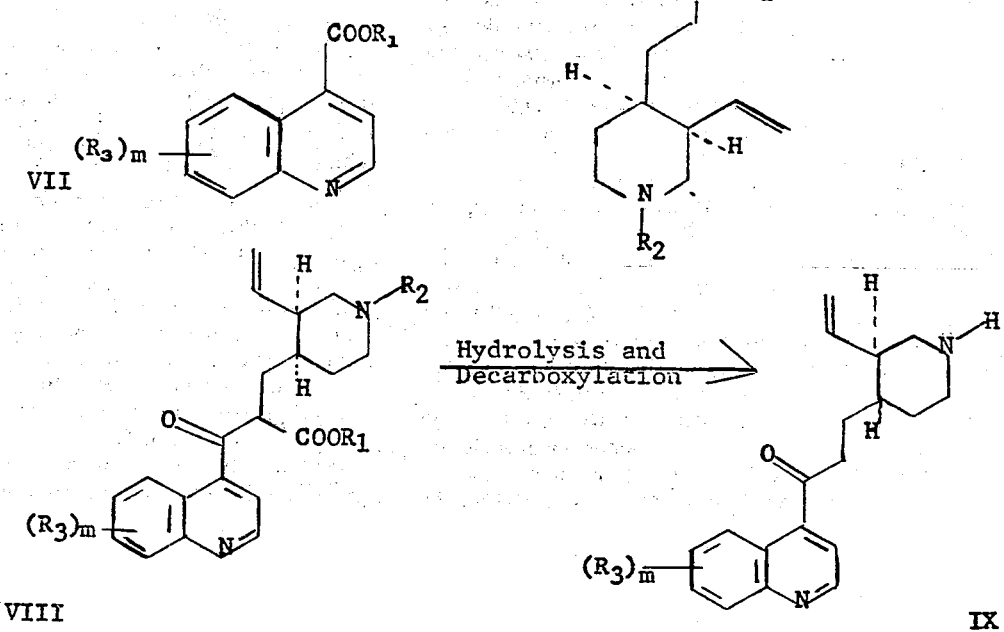

antipodes or racemates thereof wherein $R_1$ and $R_2$ are as previously described, $R_3$ is hydrogen, hydroxy, halogen, lower alkyl, lower alkoxy or methylenedioxy, and $m$ is 0, 1 or 2.

In Reaction Scheme III the cinchoninic acid lower alkyl esters of Formula VII, which are known or are analogs of known compounds readily obtained by known procedures, are reacted in the presence of a base, for example, alkaline metal alkoxides, such as sodium methoxide, sodium ethoxide, potassium tertiary butoxide and the like, with the cis 3-(1-acyl-3-vinyl-4-piperidine) propionic acid esters of Formula Ia, antipodes or racemates thereof, which are known compounds or are analogs of known compounds readily obtained by known procedures, or by the procedure hereinbefore described in Schemes I and II to yield the corresponding cis α-(1-acyl-3-vinyl-4-piperidylmethyl)-β-oxo-4-quinolinepropionic acid esters of Formula VIII. The reaction is conveniently conducted at reflux temperatures; however, lower temperatures may also be employed. An inert solvent, for example, ethers such as tetrahydrofuran, dioxane and the like, may also be conveniently employed.

The conversion of the cis α-(1-acyl-3-vinyl-4-piperidylmethyl)-β-oxo-4-quinolinepropionic acid esters of Formula VIII antipodes and racemates thereof to the corresponding cis-4-[3-(3-vinyl-4-piperidyl)-1-oxopropyl]quinolines of Formula IX is effected utilizing a hydrolyzing agent such as hydrochloric acid at reflux temperatures. Conveniently, temperatures below reflux may also be utilized.

The conversion of the compounds of formula IX to the desired end products is illustrated by Reaction Scheme IV.

Reaction Scheme IV

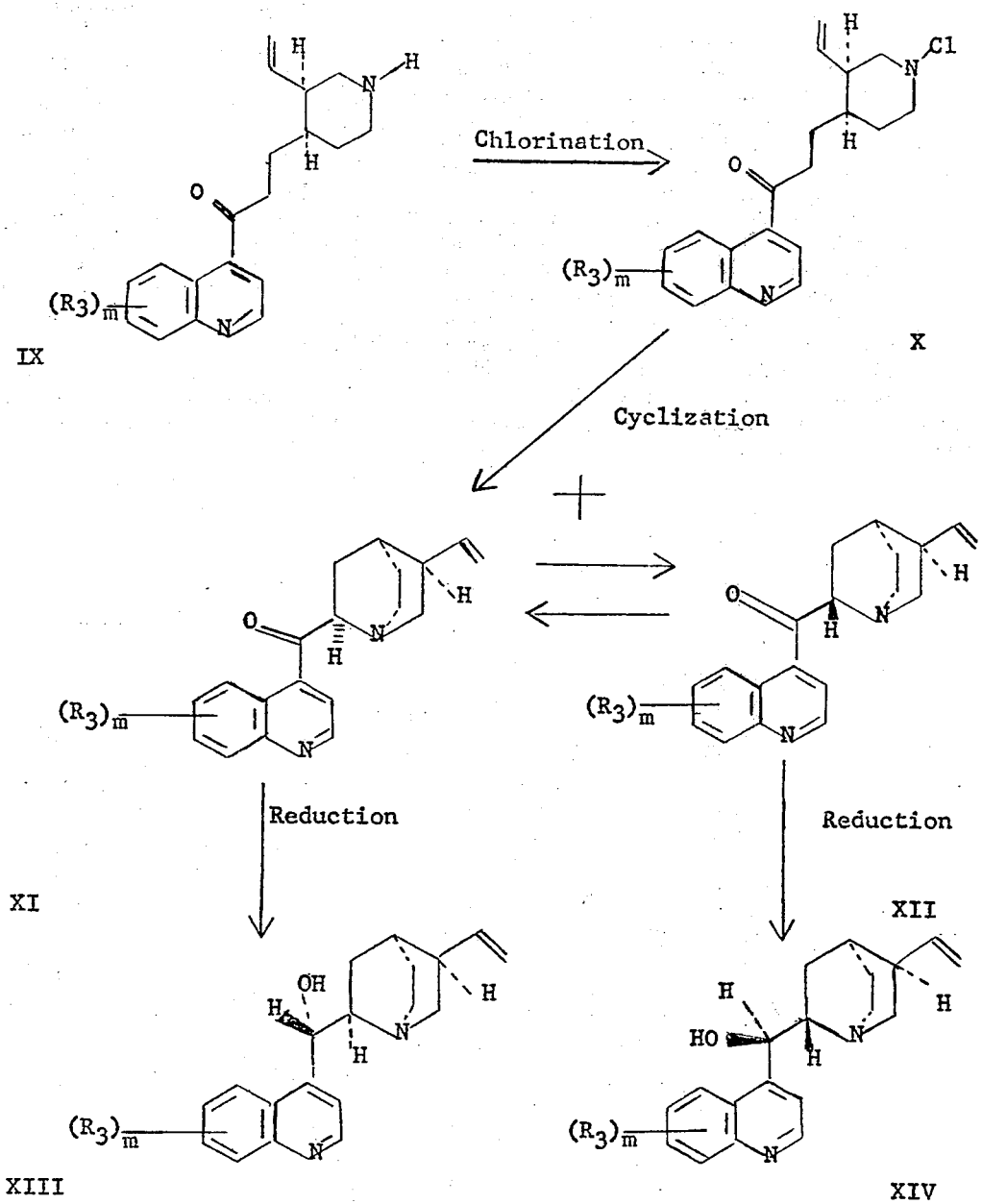

antipodes and racemates thereof wherein $R_3$ and $m$ are as previously described.

In Reaction Scheme IV, the cis 4-[3-(3-vinyl-4-piperidyl)-1-oxopropyl]quinolines of formula IX, antipodes or racemates thereof, are converted to the corresponding cis 4-[3-(1-chloro-3-vinyl-4-piperidyl)-1-oxopropyl]quinolines of formula X, utilizing a chlorinating agent such as sodium hypochlorite, N-chlorosuccinimide or the like. The chlorination is suitably carried out at room temperature or above, preferably at a temperature between 20° and 50°C. Moreover, the chlorination can be suitably carried out in the presence of an inert organic solvent, for example, a hydrocarbon such as benzene, a halogenated hydrocarbon such as dichloromethane or chlorform, or an ether such as ether or dioxane.

The cis 4-[3-(1-chloro-3-vinyl-4-piperidyl)-1oxopropyl] quinolines of formula X, antipodes or racemates thereof, are converted to the corresponding epimeric 4-[5(R)-vinyl-4-(S)-quinuclidin-2(R)-ylcarbonyl]-quinolines of formula XI, antipodes or racemates thereof, and 4-[5(R)-vinyl-4(S)-quinuclidin-2-(S)-ylcarbonyl]quinolines of formula XII, antipodes or racemates thereof, under acidic conditions, utilizing a cyclizing agent. Exemplary of such agents are inorganic or organic acids such as mineral acids, for example, phosphoric acid and sulfuric acid; alkanoic acids, for example, acetic acid, trichloroacetic acid; and mixtures thereof, for example, acetic/sulfuric acid. The reaction is conveniently carried out at room temperature or above, preferably at a temperature between 20°C. and 50°C. Moreover, the cyclization can be suitably carried out in the presence of an inert solvent of the type previously described. As mentioned above, the cyclization yields a mixture of the epimeric compounds of Formulas XI and XII, which can be reacted further as such or can be separated into the respective epimers utilizing methods such as crystallization, and the like, and such epimer reacted separately.

The conversion of the 4-[5(R)-vinyl-4(S)-quinuclidin-2(R)-ylcarbonyl]quinolines of Formula XI antipodes or racemates thereof to $\alpha$(S)-[5(R)-vinyl-4(S)-quinuclidin-2(R)-yl]-4-quinolinemethanols of Formula XIII antipodes or racemates thereof, respectively, is carried out utilizing a stereoselectively reducing agent, for example, a dialkylaluminum hydride, such as diisobutylaluminum hydride or the like. The reduction is suitable carried out at room temperature; however, temperatures above or below room temperature may be employed. It is preferred to employ a temperature between 20°C and 50°C. The reduction can be conveniently conducted in the presence of an inert organic solvent, for example, a hydrocarbon such as benzene or toluene, or an ether such as diethylether, tetrahydrofuran or the like.

The conversion of the compounds of Formula XI or their racemates to those of Formula XIII, antipodes or racemates thereof, respectively, can also be effected utilizing a hydrogenation agent such as aluminum in methanol, sodium isopropoxide in toluene, sodium or potassium borohydride in methanol, ethanol, isopropanol or tetrahydrofuran, lithium aluminum hydride, aluminum hydride, chloroaluminum hydride, dichloroaluminum hydride, bromoaluminum hydride in ether, tetrahydrofuran, dioxane or the like.

The conversion of the 4-[5(R)-vinyl-4(S)-quinuclidin-2(S)-ylcarbonyl]quinolines of formula XII, antipodes or racemates thereof, to the $\alpha$(R)-[5(R)-vinyl-4(S)-quinuclidin-2(S)-yl]-4-quinolinemethanols of formula XIV, antipodes or racemates thereof, respectively, is carried out according to the procedures described for the conversion of the compounds of formula XI.

The cis and trans 2-(1-acyl-3-vinyl-4-piperidine)acetic acid esters are used as illustrated in Reaction Scheme V for 2-(1-acyl-3(R)-vinyl-4(S)-piperidine)acetic acid ester.

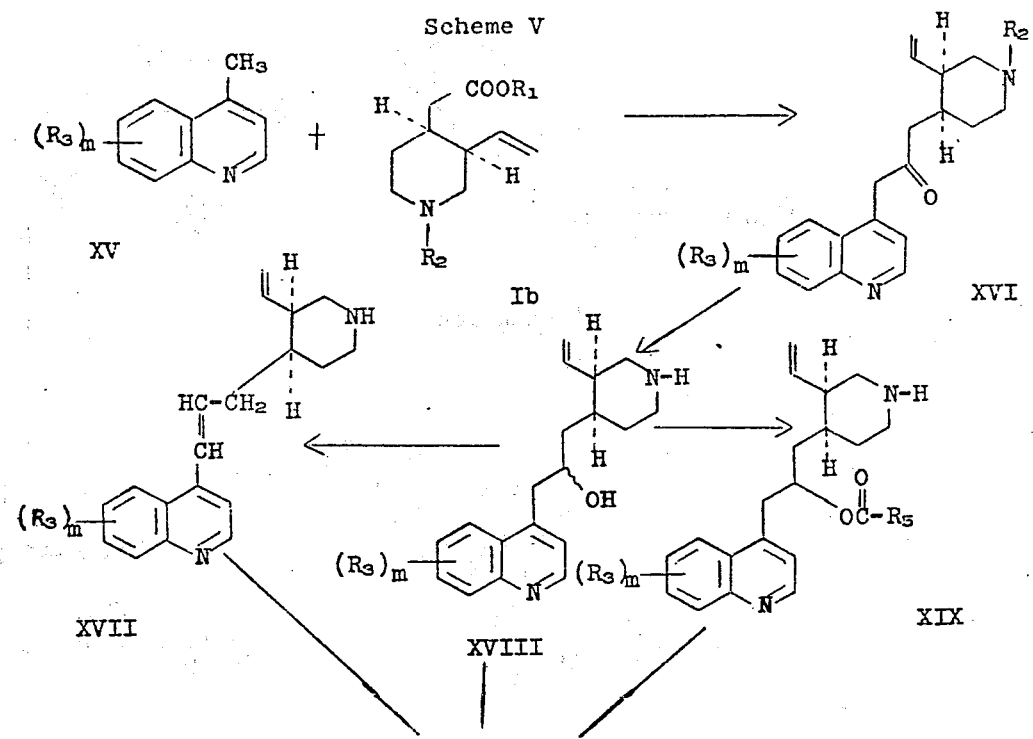

Scheme V

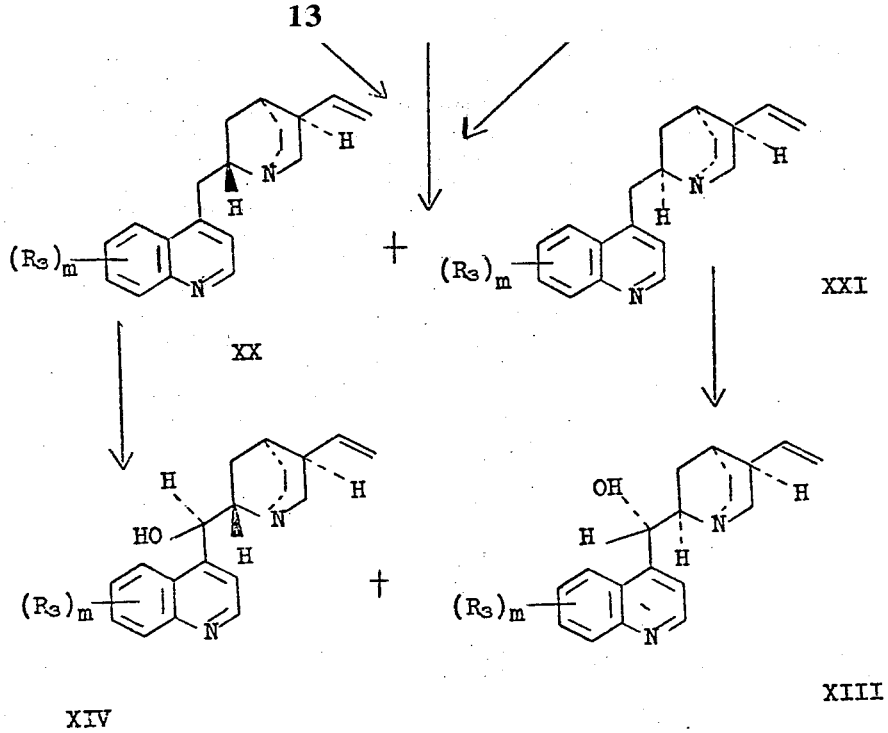

wherein $R_1$, $R_2$, $R_3$ and $m$ as previously described, and $R_5$ is lower alkyl, aryl or ar-lower alkyl.

In Reaction Scheme V, 4-methyl-quinolines of Formula XV which are known compounds or are analogs of known compounds readily obtained by known procedures, are condensed with 1-acyl-3(R)-vinyl-4-(S)-piperidineacetic acid ester of Formula Ib, antipode or its racemate which are known compounds, or are analogs of known compounds readily obtained by known procedures, or are prepared as hereinafter described, in the presence of a base, for example, sodium hydride, an alkali metal alkoxide such as sodium methoxide, or a lithium dialkylamide such as lithium diisoproylamide to yield 4-{3-[1-acyl-3(R)-vinyl-4(S)-piperidyl]-2-oxopropyl} quinoline of formula XVI, antipode or its racemate, respectively. The condensation is suitably carried out at room temperature; however, temperatures above or below room temperature may be employed. Preferably, the condensation is conducted at a temperature within the range of about −70° and about 50°C. Moreover, the condensation can be suitable carried out in the presence of an inert organic solvent, for example, a hydrocarbon, such as benzene, a halogenating hydrocarbon such as dichloromethane or chloroform, or an ether, such as ether, tetrahydrofuran or dioxane.

The 4-{3-[1-acyl-3(R)-vinyl-4(S)-piperidyl]-2-oxopropyl} quinoline of formula XVI, antipode or its racemate is converted to the mixture of epimeric 4-{3-[3(R)-vinyl-4(S)-piperidyl]-2ϵ-hydroxypropyl}quinolines of formula XVIII, their antipodes or racemates by simultaneous deacylation, if necessary, and reduction. The deacylation and reduction are conveniently effected utilizing a reducing agent, for example, diisobutylaluminum hydride, sodium aluminum hydride and the like, in an inert organic solvent, for example, a hydrocarbon such as benzene or toluene, ether, tetrahydrofuran and the like. The deacylation and reduction are suitably carried out at room temperature or below, preferably at a temperature within the range of about −70° to about 25°C. If desired, the compound of formula XVIII can be esterified to the corresponding mixture of epimeric 4-{3-[3(R)vinyl-4(S)-piperidyl]-2ϵ-acyloxypropyl}quinolines of formula XIX, their antipodes or racemates utilizing known procedures, for example, reaction with the corresponding organic acid in the presence of a catalyst, such as boron trifluoride. Alternatively, if desired, the compound of Formula XVIII can be converted to cis and trans 4-{3-[3(R))vinyl -4 (R)-piperidyl]prop-1-enyl}quinolines of Formula XVII their antipodes or racemates utilizing a dehydrating agent such as thionyl chloride, phosphorus oxychloride, phosphorus pentachloride and the like, in the presence of an organic base, for example, a tertiary amine such as pyridine, triethylamine and the like, at about temperature within the range of aabout 0° to about room temperature.

The cyclization of epimeric 4-{3-[3(R)-vinyl-4(S)-piperidyl]-2ϵ-hydroxy(or acyloxy)propyl}quinolines of Formulas XVIII and XIX, their antipodes or racemates, respectively, and cis and trans 4-{3-[3(R)-vinyl-4(R)-piperidyl]prop-l-enyl}quinolines of Formula XVII, their antipodes or racemates to 4-{α-[5(R)-vinyl-4(S)-quinuelidin-2(S) and 2(R)-yl]-methyl}quinolines of Formulas XX and XXI, their antipodes or racemates is carried out utilizing a cyclizing agent, for example, an organic acid, such as glacial acetic acid or the like. The cyclization is suitable carried out at room temperature; however, temperatures above or below room temperature may also be employed. It is preferred to employ a temperature within the range of about 25° to about 100°C. Moreover, the cyclization can be conveniently conducted in the presence of an inert organic solvent, for example, a hydrocarbon such as benzene or toluene, or an ether, such as diethyl ether or tetrahydrofuran.

The hydroxylation of the compounds of Formula XX and XXI or their racemates to α(R)-[5(R)-vinyl-4(S)-quinuclidin-2(S)-yl]-4-quinolinemethanol of Formula XIV, its antipode or racemate and α(S)-[5(R)-vinyl-4(S) quinucldin-2(R)-yl]-4-quinolinemethanol of Formula XIII, its antipode or racemate, respectively, is carried out, for example, in the presence of molecular oxygen in a strongly basic solution.

The compounds of formula II are know compounds or can be prepared as follows:

Cis-compounds of formula II are known. The trans-compounds of the formula

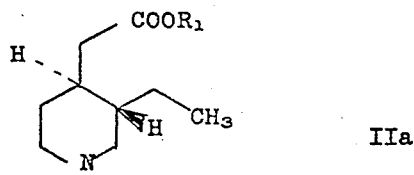

are new and can be prepared by the following sequence:

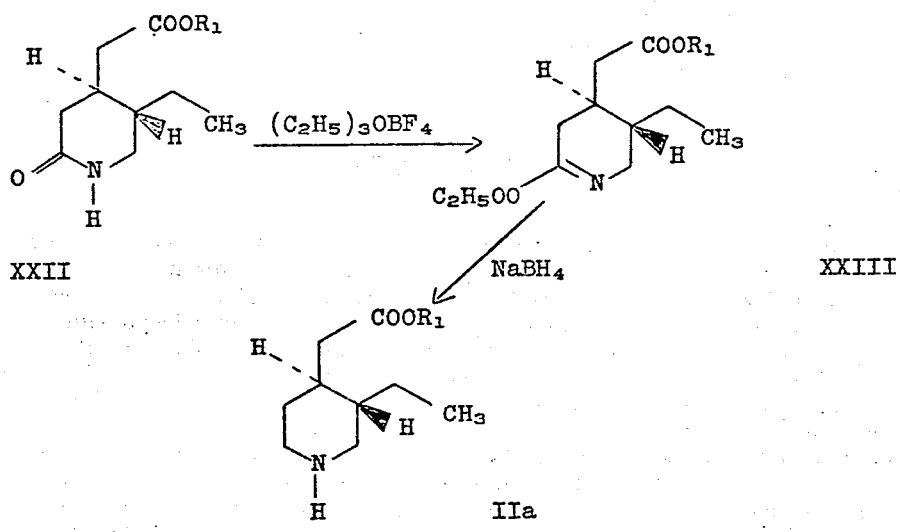

as further described in the Examples. The compound of formula XXII are known compounds.

The compounds of Formulas XIII and XIV and their pharmaceutically acceptable acid addition salts possess antimalarial and antiarrhythmic properties and are therefore usful as antimalarial and antiarrhythmic agents. Their pharmacologically useful antiarrhythmic activity is demonstrated in warm-blooded animals utilizing standard procedures, for example, the test compound is administered to prepared mongrel dogs. The chest cavity of the experimental animal previously anesthetized using a combination of sodium barbitol, 300 mg/kg. and pentobarbital, 15 mg/kg., i.v., is opened up through the third right interspace under artificial respiration and the pericardium is cut and sutured to the wall of the thorax so as to maintain the heart in a pericardial cradle throughout the course of the test procedure. Arterial pressure is monitored by inserting a polyethylene cannula into the aorta via the left carotid artery and is measured with an appropriate Statham pressure transducer. During the course of the experiment, electrical activity of the heart is viewed both on an oscilloscope and recorded on a Sanborn polyviso using standard EGG lead II. The heart is also observed visually. The antiarrhythmic assay of the test drug is undertaken using a modification of the method of Scherf and Chick, Circulation, 3,764,769 (1951). A dripping of 1 percent solution of acetycholine is applied to the sinus node and the atrium is irritated by pinching with a pair of forceps. This procedure produces a continuous atrial arrhythmia which mostly consists of atrial fibrillation. Since hypokalemia produces a susceptibility to atrial fibrillation (Leveque, Arch. Int. Pharmacodyn, 297–207,1964), 2 units/kg. of insulin is administered 30 minutes before the start of the acetylcholine drip. Once atrial fibrillation is established, there is a ten-minute waiting period before the test drug is administered. The test drugs are administered intravenously at the rate of 1mg/kg/minute until normal sinus rhythm appears or until 30 mg/kg. of drug is administered.

When racemic 7'-methoxy-dihydrocinchonidinone is utilized as the test substance at a dosage of about 4.4 mg/kg., i.v., an antifibrillatory effect is observed for more than 60minutes.

The pharmacologically useful antimalarial activity of the aforementioned compounds is demonstrated in warm-blooded animals using standard procedures, for example, the test substance is administered to albino mice in variable amounts. Albino mice are inoculated with about 10 million red cells infected with P. Bergei. Treatment is started on the first day after inoculation, and the drug is administered "per os" during 4 consecutive days. On the seventh day of infection, smears are made, stained with giemsa and microscopically examined for P. Bergei.

When racemic 7'-methoxy-dihydrocinchonidine dihydrochloride and racemic 7'-methoxy-dihydrocinchonine dihydrochloride are utilized as the test substance at dosages in the range of 125 mg/kg. to about 250 mg/kg., the microscopical examination of the blood smears is free of P. Berghei (negative). The compounds of Formulas Ic, IIc, Vc and VIc and the pharmaceutically acceptable acid addition salts have effects quantitatively similar, for example, to those of quinine and quinidine of known therapeutic uses and properties. Thus, the compounds of the invention demonstrate a pattern of activity associated with antimalarials and antiarrhythmics of known efficacy and safety.

The compounds of Formulas XIII and XIV form acid addition salts and such salts are also within the scope of this invention. Thus, the aforementioned compounds form pharmaceutically acceptable addition salts with, for example, both pharmaceutically acceptable organic cand inorganic acids, such as acetic acid, succinic acid, formic acid, methanesulfonic acid, p-toluene-sulfonic acid, hydrochloric acid, nitri acid, phosphoric acid, sulfuric acid and the like.

The products of the invention can be incorporated into standard pharmaceutical dosage forms, for example, they are useful for oral or parenteral application with the usual pharmaceutical adjuvant materials, e.g., organic or inorganic inert carrier materials such as water, gelatin, lactose, starch, magneisum stearate, talc, vegatable oils, gums, polyalkyleneglycols, and the like. The pharmaceutical preparations can be employed in a solid form, e.g., as tablets, troches, suppositories, capsules, or in liquid form, e.g., as solutions, suspensions or emulsions. The pharmaceutical adjuvant material can include preservatives, stabilizers, wetting or emulsifying agents, salts to change the osmotic pressure or to act as buffers. They can also contain other therapeutically active materials.

Furthermore, the compounds of the Formulas XIII and XIV can be utilized as flavoring agents in beverages in the same manner as quinine is now used for this purpose.

The quantity of active medicament which is present in any of the above-described dosage forms is variable. The frequency with which any such dosage form will be administered will vary, depending upon the quantity of active medicament present therein and the needs and requirements of the pharmacological situation.

Due to the possible different spatial arrangements of their atoms, it is to be understood that the compound of this invention may be obtained in more than one possible stereoisomeric form. The novel compounds, as described and claimed, are intended to embrace all such isomeric forms. Accordingly, the examples included herein are to be understood as illustrative of particular mixtures of isomers or single isomers and not as limitations upon the scope of the invention. All temperatures are in degrees centigrade, unless otherwise mentioned.

The following examples further illustrate the invention. All temperatures are in degrees Centigrade, unless otherwise mentioned.

EXAMPLE 1

Preparation of rac. cis 3-(1-chloro-3-ethyl-4-piperidine)propionic acid ethyl ester A. To a solution of 1.064 g. of racemic cis 3-(3-ethyl-4-piperidine)propionic acid ethyl ester in 30 ml. of ether was added 30 ml. of a 16.9% aqueous solution of sodium hypochlorite. The mixture was shaken at room temperature. In intervals of 1 hour the aqueous layer was separated and fresh sodium hypochlorite solution (30 ml.) was added. After 4.5 hours, 100 ml. of benzene was added to the mixture. The organic layer was separated and washed successively with water (2 ×), 3N aqueous hydrochloric acid (3 ×) and water (3 ×). After drying over sodium sulfate and evaporating under reduced pressure 0.90 g. of liquid rac. cis 3-(1-chloro-3-ethyl-4-piperidine)propionic acid ethyl ester was obtained.

B. To a stirred suspension of 11 g. of N-chlorosuccinimide in 200 ml. of anyhydrous ether was added in a nitrogen atmosphere a solution of 15 g. of rac. cis 3-(3-ethyl-4-piperidine)propionic acid ethyl ester in 100 ml. of anhydrous ether. After continued stirring for 1 hour at room temperature, the mixture was successively washed with water (3 ×), 2.5N aqueous sulfuric acid (2 ×) and water. The ethereal solution was dried over anhydrous sodium sulfate. Evaporation of the solvent under reduced pressure gave 18 g. of liquid racemic cis 3-(1-chloro-3-ethyl-4-piperidine) propionic acid ethyl ester.

EXAMPLE 2

Preparation of rac. cis 3[1-benzoyl-3-(2-chloroethyl)-4-piperidine]propionic acid ethyl ester 5 Grams of racemic cis 3-(1-chloro-3-ethyl-4-piperidine) propionic acid ethyl was dissolved in 150 ml. of trifluoroacetic acid at 0°. The resulting clear solution was transferred to a quartz flask, purged with dry nitrogen for 30 minutes and then irradiated at 10° with a 200W-Hanovia high-pressure mercury lamp. At intervals, samples were removed and the reaction was continued until a negative starch-iodide test was obtained. After 5 hours, the solvent was removed at 35° under reduced pressure. Benzene was added to residue residue and evaporated under reduced pressure. This procedure was repeated several times. To a stirred solution of 40 g. of the crude rac. cis 3-[3-(2-chloroethyl)-4-piperidine]propionic acid ethyl ester trifluoroacetate and 26 g. of benzoyl chloride in 400 ml. of benzene was added over a period of 2 hours a saturated aqueous solution of potassium carbonate until the pH reached 9. Stirring was continued for 1 hour. After the addition of 200 ml. of benzene, the mixture was washed successively with 6N aqueous sodium hydroxide (3×), water, 3N aqueous hydrochloric acid and water. The organic layer was separated and dried over anhydrous sodium sulfate. Evaporation to dryness gave 30 g. of oily material, which was chromatographed on 650 g. of silica gel with benzene-ethyl acetate (9:1) as the liquid phase to give 22.3 g. of 96.3% pure racemic cis 3-[1-benzoyl-3-(2-chloroethyl)-4-piperidine]propionic acid ethyl ester. Yield 87%.

The chromatographed material solidified on standing at room temperature and after washing with pentane-ether crystalline racemic cis-3-[1-benzoyl-3-(2-chloroethyl)-4-piperidine]propionic acid ethyl ester was obtained, m.p. 53°–55°.

Anal. Calcd. for $C_{19}H_{26}ClNO_3$ (351.88); C, 64,85; H, 7.45; N, 3.98; Found: C, 65.01; H, 7.54; N, 3.99.

EXAMPLE 3

Preparation of rac. cis 3-(1-benzoyl-3-vinyl-4-piperidine) propionic acid ethyl ester A. A solution of 3.5 g. of rac. cis 3-[1-benzoyl-3-(2-chloroethyl)-4-piperidine]propionic acid ethyl ester and 2.3 g. of sodium iodide in 120 ml. of methyl ethyl ketone was kept at reflux temperature for 44 hours. The mixture in which a precipitate had formed was diluted with 50 ml. of water and 100 ml. of ether. The organic layer was separated, washed with water, diluted with benzene (100 ml.), dried over anhydrous sodium sulfate, and evaporated to dryness to give 4 g. of liquid rac. cis 3-[1-benzoyl-3-(2-iodoethyl)-4-piperidine]propionic acid ethyl ester. This was dissolved in 120 ml. of anhydrous pyridine, and after the addition of 2.5 g. of silver fluoride, the mixture was stirred at room temperature for 24 hours. Ether (800 ml.) was added, and the black precipitate was removed by filtration. The filtrate was washed with 3N aqueous hydrochoric acid (3 ×)

and water, dried over anhydrous sodium sulfate and evaporated to dryness. The residue was distilled under a pressure of 0.015 mmHg. to give two fractions: at 120°C. 0.615 g. of 82% pure and at 150°C. 0.990 g. of 71% pure liquid rac. cis 3-(1-benzoyl-3-vinyl-4-piperidine)propionic acid ethyl ester: yield 38%.

B. A mixture of 0.5 g. of rac. cis 3-[1-benzoyl-3-(2-chloroethyl)-4-piperidine]propionic acid ethyl ester and glass powder was heated at 190° under a pressure of 0.025 mm. for 5 hours. The black reaction mixture was dissolved in dichloromethane, the glass powder was removed by filtration, and the filtrate was evaporated to dryness. The residue (350 mg.) was distilled at 0.015 mmHg. and 150°C., to give 99 mg. of liquid 78% pure rac. cis 3-(1-benzoyl-3-vinyl-4-piperidine)propionic acid ethyl ester.

EXAMPLE 4

Preparation of
3-[1-benzoyl-3(S)-(2-chloroethyl)-4(S)-piperidine]-propionic acid ethyl ester The mono-1-tartrate of 3-[3(S)-ethyl-4(S)-piperidine]propionic acid ethyl ester (8.9 g.) was treated with excess 2N aqueous potassium carbonate. The liberated free base was extracted into dichloromethane. The combined organic extract was dried over potassium carbonate and evaporated to dryness under reduced pressure to give 5 g. of 3-[3(S)-ethyl-4(S)-piperidine]propionic acid ethyl ester. A solution of the free base in 35 ml. of anhydrous ether was added in a nitrogen atmosphere to a stirred suspension of 3.4 g. of N-chlorosuccinimide in 70 ml. of anhydrous ether. After continued stirring for 1 hour at room temperature, the mixture was successively washed with water (3 ×), 2.5N aqueous sulfuric acid (2 ×) and water. The ethereal solution was dried over anhydrous sodium sulfate. Evaporation of the solvent under reduced pressure gave 5.1 g. of liquid 3-[1-chloro-3(S)-ethyl-4(S)-piperidine]propionic acid ethyl ester. This N-chloroamine was dissolved in 150 ml. of trifluoroacetic acid at 0°. The resulting clear solution was transferred to a quartz flask, purged with dry nitrogen for 30 minutes and then irradiated at 14° with a 200W-Hanovia high-pressure mercury lamp. At intervals, samples were removed and the reaction was continued as long as positive starch-iodine test was obtained. After 3 hours, the solvent was removed at 35° under reduced pressure. Benzene was added to the residue and evaporated under reduced pressure. This procedure was repeated several times. To a stirred solution of thus obtained 3-[3(S)-(2-chloroethyl)-4(S)-piperidine]propionic acid ethyl ester trifluoroacetate (11.9 g.) and 8 g. of benzoylchloride in 100 ml. of benzene was added slowly a saturated aqueous solution of potassium carbonate until the mixture reached pH 9. Stirring was continued for 90 minutes. After the addition of 100 ml. of benzene, the mixture was washed successively with 6N aqueous hydroxide (3 ×), water, 3N aqueous hydrochloric acid and water. The organic layer was separated and dried over anhydrous sodium sulfate. Evaporation to dryness gave 8.4 g. of oily material which was chromatographed on 250 g. of silica gel. Elution with 95:5, 9:1 and 8:2 mixtures of benzene and ethylacetate gave 5.95 g. of liquid 87% pure 3-[1-benzoyl-3(S)-(2-chloroethyl)-4(S)-piperidine]propionic acid ethyl ester. Yield 60%. This product was distilled twice at 0.015 mmHg and 160°C., to give 2 g. of 98.9% pure 3-[1-benzoyl-3(S)-(2-chloroethyl)-4(S)-piperidine]-propionic acid ethyl ester $[\alpha]_D^{22} = -20.0°$ (c = 0.99, methanol).

EXAMPLE 5

Preparation of
3[1-benzoyl-3(S)-vinyl-4(S)-piperidine]propionic acid ethyl ester A solution of 1.9 g. of 3-[1-benzoyl-3(S)-(2-chloroethyl)-4(S)-piperidine]propionic acid ethyl ester and 1.22 g. of sodium iodide in 60 ml. of methyl ethyl ketone was kept at reflux temperature for 50 hours. The mixture in which a precipitate had formed was diluted with 30 ml. of water and 50 ml. of ether. The organic layer was separated, washed with water, diluted with benzene (50 ml.), dried over anhydrous sodium sulfate and evaporated to dryness to give 2.2 g. of liquid crude 3-[1-benzoyl-3(S)-(2-iodoethyl)-4(S)-piperidine]propionic acid ethyl ester. This was dissolved in 60 ml. of anhydrous pyridine, and after the addition of 1.3 g. of silver fluoride, the mixture was stirred at room temperature for 20 hours. Ether (400 ml.) was added and the black precipitate was removed by filtration. The filtrate was washed with 3N aqueous hydrochloric acid (3 ×) and water, dried over anhydrous sodium sulfate and evaporated to dryness. The liquid residue (0.82 g.) was distilled at 0.015 mmHg and 118°C. to give 540 mg. of 75% pure 3-[1-benzoyl-3(S)-vinyl-4(S)-piperidine]-propionic acid ethyl ester.

An analytical sample of 99.5% purity was obtained by preparative gas chromatography, $[\alpha]_D^{25}$ −35.4° (c=1.12, methanol).

EXAMPLE 6

Preparation of
3-[1-benzoyl-3(R)-(2-chloroethyl)-4(R)-piperidine]-propionic acid ethyl ester The mono-d-tartrate of 3-[3(R)-ethyl-4(R)-piperidine]propionic acid ethyl ester (15 g.) was treated with excess 2N aqueous potassium carbonate, the liberated free base was extracted into dichloromethane. The combined organic extract was dried over anhydrous sodium sulfate and evaporated to dryness under reduced pressure to give 8.8 g. of 3-[3(R)-ethyl-4(R)-piperidine]propionic acid ethyl ester. A solution of the free base in 60 ml. of anhydrous ether was added in a nitrogen atmosphere to a stirred suspension of 6.0 g. of N-chlorosuccinimide in 120 ml. of anhydrous ether. After continued stirring for 1 hour at room temperature, the mixture was successively washed with water (3 ×), 2.5N aqueous sulfuric acid (2 ×) and water. The ethereal solution was dried over anhydrous sodium sulfate. Evaporation of the solvent under reduced pressure gave 9 g. of liquid 3-[1-chloro-3(R)-ethyl-4(R)-piperidine]propionic acid ethyl ester. This N-chloroamine was dissolved in 150 ml. of trifluoroacetic acid at 0°. The resulting clear solution was transferred to a quartz flask, purged with dry nitrogen for 30 minutes and then irradiated at 10° with a 200W-Hanovia high-pressure mercury lamp. At intervals, samples were removed and the reaction was continued as long as a positive starch-iodine test was obtained. After 5 hours, the solvent was removed at 35° under reduced pressure. Benzene was added to the residue and evaporated under reduced pressure. This procedure was repeated several times. To a stirred solution of 3-[3(R)-(2-chloroethyl)-4(R)-piperidine]propionic acid ethyl ester trifluoroacetate (22 g.) thus obtained and 15 g. of benzoylchloride in 150 ml. of benzene was added slowly a saturated aqueous solution of potassium carbonate until the mixture reached pH 9. Stirring was continued for 1 hour. After the addition of 200 ml. of benzene, the mixture was washed successively with 6N aqueous sodium hydroxide (3 ×), water, 3N aqueous hydrochloric acid and water. The organic layer was separated and dried over anhydrous sodium sulfate. Evaporation to dryness gave 18 g. of oily material which was chromatographed on 650 g. of silica gel. Elution with 9:1 mixture of benzene and ethyl acetate gave 11.1 g. of liquid 97.5% pure 3-[1-benzoyl-3(R)-(2-chloroethyl)-4(R)-piperidine]propionic acid ethyl ester. Yield 74%. Analytical sample of 98.6% purity was obtained by distillation at 0.018 mmHg. and 150°C. $[\alpha]_D^{22} = +20.2°$ (c = 1.09, methanol).

EXAMPLE 7

Preparation of 3-[1-benzoyl-3(R)-vinyl-4(R)-piperidine]propionic acid ethyl ester A solution of 1.8 g. of 3-[1-benzoyl-3(R)-(2-chloroethyl)-4(R)-piperidine]propionic acid ethyl ester and 1.2 g. of sodium iodide in 60 ml. of methyl ethyl ketone was kept at reflux temperature for 44 hours. The mixture in which a precipitate had formed was diluted with 30 ml. of water and 50 ml. of ether. The organic layer was separated, washed with water, diluted with benzene (50 ml.), dried over anhydrous sodium sulfate and evaporated to dryness to give 2.3 g. of liquid crude 3-[1-benzoyl-3(R)-(2-iodoethyl)-4(R)-piperidine]propionic acid ethyl ester. This was dissolved in 60 ml. of anhydrous pyridine, and after the addition of 1.29 g. of silver fluoride the mixture was stirred at room temperature for 15 hours. Ether (400 ml.) was added and the black precipitate was removed by filtration. The filtrate was washed with 3N aqueous hydrochloric acid (3 ×) and water, dried over anhydrous sodium sulfate and evaporated to dryness. The liquid residue (1.23 g.) was distilled under a pressure of 0.015 mmHg. A fraction (560 mg.) distilling at 100° (oil bath temperature) contained 94% pure 3-[1-benzoyl-3(R)-vinyl-4(R)-piperidine] propionic acid ethyl ester. By raising the oil bath temperature to 115°, 320 mg. of a second fraction containing 87% pure 3-[1-benzoyl-3(R)-vinyl-4(R)-piperidine]propionic acid ethyl ester was obtained. Total yield 50%. An analytical sample was obtained by preparative gas chromatography, $[\alpha]_D^{25} = +35.8°$ (c = 0.97, methanol).

EXAMPLE 8

Preparation of rac. cis 3-(1-benzoyl-3-vinyl-4-piperidine) propionic acid ethyl ester A solution containing 41.9 g. of rac. cis 3-[1-benzoyl-3-(2-chloroethyl)-4-piperidine]propionic acid ethyl ester in 600 ml. of methanol was combined with 600 ml. of 1N sodium hydroxide and allowed to stand at room temperature for 36 hours. The methanol was removed. The residue was rendered acidic by the addition of 3N hydrochloric acid and thereafter was extracted with dichloromethane. The combined organic layer was dried over sodium sulfate and evaporated under reduced pressure to give 39.5 g. of rac. cis 3-[1-benzoyl-3-(2-chloroethyl)-4-piperidine] propionic acid. A solution of this residue in 600 ml. of anhydrous benzene was added to a solution containing 29 g. of potassium-t-butoxide in 600 ml. of anhydrous dimethylsulfoxide. The mixture was stirred under an atmosphere of nitrogen for 15 hours at 70°. After removal of benzene under reduced pressure, 500 ml. of 1N sodium hydroxide was added, and the mixture was extracted with dichloromethane. The aqueous solution was acidified with concentrated hydrochloric acid and extracted with three portions of an ether-benzene mixture. The combined organic layers were washed with water, dried over sodium sulfate and evaporated under reduced pressure. The residue was dissolved in 320 ml. of anhydrous ethanol. 4.8 ml. of concentrated sulfuric acid was added and the solution was refluxed for 18 hours. Thereafter, the solution was concentrated under reduced pressure to about 100 ml., diluted with water and extracted three times with ether-benzene. The combined organic layers were washed successively with water, saturated aqueous sodium bicarbonate solution and water, dried over sodium sulfate and evaporated under reduced pressure to yield 31.3 g. of rac. cis 3-(1-benzoyl-3-vinyl-4-piperidine)propionic acid ethyl ester. Low boiling impurities were removed by distillation at 40° and a pressure of 0.2 mmHg. to give 27.5 g. of rac. cis 3 -(1-benzoyl-3-vinyl-4-piperidine)propionic acid ethyl ester, 70% yield.

EXAMPLE 9

Preparation of rac. cis-1-chloro-3-ethyl-4-piperidineacetic acid methyl ester from rac. cis-3-ethyl-4-piperidineacetic acid methyl ester To a stirred suspension of 4.8 g. of N-chlorosuccinimide in 120 ml. anhydrous ether under nitrogen was added 5.55 g. of racemic cis-3-ethyl-4-piperidineacetic acid methyl ester, and stirred for 1 hour. After dilution with 3 liters of ether, the reaction mixture was washed in sequence with three 100 ml. portions of water, 2–100 ml. portions of 5N potassium carbonate, two 100 ml. portions of water, two 100 ml. portions of 2.5N sulfuric acid and two 100 ml. portions of water. The ethereal solution was then dried over anhydrous magnesium sulfate, filtered and evaporated to give 5.6 g. of the pure oily racemic cis-1-chloro-3-ethyl-4-piperidineacetic acid methyl ester, which was immediately reacted further in accordance with Example 10.

EXAMPLE 10

Preparation of rac. cis-1-benzoyl-3-(2-chloroethyl)-4-piperidineacetic acid methyl ester from rac. cis-1-chloro-3-ethyl-4-piperidineacetic acid methyl ester A solution of 5.6 g. of racemic cis-1-chloro-3-ethyl-4-piperidineacetic acid methyl ester in 150 ml. of trifluoroacetic acid in a quartz flask was flashed with nitrogen and cooled in an ice-bath for 30 minutes. Under a continuing stream of nitrogen and cooling, the mixture was irradiated with 200 Watt Hanovia lamp for 50 minutes. Evaporation in vacuo gave crude racemic cis-3-(2-chloroethyl)-4-piperidineacetic acid methyl ester trifluoroacetate. To the stirred solution of the trifluoroacetate salt in 450 ml. of benzene was added first 5.94 g. of benzoyl chloride and then slowly dropwise 5N potassium carbonate until pH ~ 9 was reached. Stirring was then continued for 2 hours, whereupon the reaction mixture was diluted with 3 liters of benzene and extracted in sequence with three 100 ml. portions of 6N sodium hydroxide, three 100 ml. portions of water, two 100 ml. portions of 3N hydrochloric acid and water. The benzene solution was then dried over anhydrous sodium sulfate and evaporated. The residue was dissolved in methanol, refluxed for 15 minutes and evaporated. The product thus obtained was chromatographed on silica-gel plates in 1:1 ether-petroleum ether system, and eluted with 3:1 chloroform-methanol mixture to give 7.01 g. of oily racemic cis-1-benzoyl-3-(2-chloroethyl)-4-piperidineacetic acid methyl ester.

EXAMPLE 11

Preparation of rac. cis-1benzoyl-3-(2-chloroethyl)-4-piperidineacetic acid from racemic cis-1-benzoyl-3-(2-chloroethyl)-4-piperidineacetic acid methyl ester To a solution of 7.24 g. of racemic cis-1-benzoyl-3-(2-chloroethyl)-4-piperidineacetic acid methyl ester in 112 ml. of methanol was added 112 ml. 1N sodium hydroxide. The mixture was stirred at room temperature for about 17 hours. Then, the methanol was removed by distillation. The residue was made acidic with 3N hydrochloric acid, and extracted with eight 200 ml. portions of methylene chloride. The extract was dried over anhydrous sodium sulfate, filtered and evaporated to give 6.85 g. of crystalline racemic cis-1-benzoyl-3-(2-chloroethyl)-4-piperidineactic acid; having a melting point of 121°-124° after recrystallization from ether.

EXAMPLE 12

Preparation of rac. cis-1-benzoyl-3-vinyl-4-piperidineacetic acid methyl ester from racemic cis-1-benzoyl-3-(2-chloroethyl)-4-piperidineacetic acid To a solution of 5.44 g. of rac. cis-1-benzoyl-3-(2-chloroethyl)-4-piperidineacetic acid in 82.5 ml. benzene, there was added 3.99 g. of potassium tert.-butoxide in 82.5 ml. dimethylsulfoxide. The reaction mixture was stirred and heated at 70° under nitrogen for 7 hours. The benzene was removed by distillation. After the addition of 82.5 ml. of 1N sodium hydroxide, the residue was extracted with five 100 ml. portions of methylene chloride. The aqueous phase was made acidic with concentrated hydrochloric acid and extracted with five 200 ml. portions of ether-benzene 1:1. The last extract was dried over anhydrous sodium sulfate, filtered and evaporated. 5.15 g. of the resulting product, composed mainly of racemic cis-1-benzoyl-3-vinyl-4-piperidineacetic acid, was used in the esterification without further purification. To a solution of the product in 90 ml. of methanol, was added 38 ml. of diazomethane solution (~ 3 g./100 ml. in ethanol/ether) and stirred 90 minutes. Then, 10 ml. of diazomethane solution was added and stirred for an additional 90 minutes. This was followed by the addition of several drops of glacial acetic acid and by evaporation to dryness. This procedure gave 5.53 g. of crude product, which was chromatographed on 54 preparative silica gel plates with ethyl acetate and eluted with 1:1 chloroform-methanol to give 2.52 g. of racemic cis-1-benzoyl-3-vinyl-4-piperidineacetic acid methyl ester, which crystallized on standing in cold and had a melting point of 57°-58° (from ether).

EXAMPLE 13

Preparation of rac. trans-1-chloro-3-ethyl-4-piperidineacetic acid ethyl ester from racemic trans-3-ethyl-4-piperidineacetic acid ethyl ester To a stirred suspension of 2.803 g. of N-chlorosuccinimide in 75 ml. of anhydrous ether under nitrogen was added 3.5 g. of racemic trans-3-ethyl-4-piperidineacetic acid ethyl ester. The resulting reaction mixture was stirred for one hour. After dilution with 2 liters of ether, the reaction mixture was washed in sequence with three 50 ml. portions of water, two 50 ml. portions of 5N potassium carbonate solution, two 50 ml. portions of water, two 50 ml. portions of 2.5N sulfuric acid and two 50 ml. portions of water. The ethereal solution was then dried over anhydrous magnesium sulfate, filtered and evaporated to give 3.9 g. of the pure oily racemic trans-1-chloro-3-ethyl-4-piperidineactic acid ethyl ester, which was immediately reacted further in accordance with Example 14.

EXAMPLE 14

Preparation of rac. trans-1-benzoyl-3-(2-chloroethyl)-4-piperidineacetic acid ethyl ester from racemic trans-1-chloro-3-ethyl-4-piperidineacetic acid ethyl ester A solution of 3.9 g. of racemic trans-1-chloro-3-ethyl-4-piperidineacetic acid ethyl ester in 150 ml. of trifluoroacetic acid in a quartz flask was flashed with nitrogen and cooled to 10°C. for 30 minutes. Under a continuing stream of nitrogen and cooling, the reaction mixture was irradiated with a 200 Watt Hanovia lamp for 3½ hours. Evaporation in vacuo gave the crude product comprising racemic trans-3-ethyl-4-piperidineacetic acid ethyl ester trifluoroacetate and racemic trans-3-(2-chloroethyl)-4-piperidineacetic acid ethyl ester trifluoroacetate. To the stirred solution of this salt in 300 ml. of benzene was added first 5.6 g. of benzoyl chloride and then slowly dropwise 5N potassium carbonate solution until pH ~ 9 was reached. Stirring was continued for 1 hour. Then, the reaction mixture was diluted with 3 liters of benzene and extracted in sequence with three 100 ml. portions of 6N sodium hydroxide, three 100 ml. portions of water, three 100 ml. portions of 1N hydrochloric acid and 100 ml. of water. The benzene solution was then dried over anhydrous sodium sulfate and evaporated. The resulting crude product was chromatographed on Brinkmann silica gel preparative plates with ether-petroleum ether 1:1 system and the separated components where eluted with 3:1 chloroform-methanol mixture. Each product was dissolved in ether. The ethereal solution was washed with 1N sodium hydroxide and water, dried over anhydrous magnesium sulfate and evaporated. The less polar product, 1.476 g., was racemic trans-1-benzoyl-3-ethyl-4-piperidineacetic acid ethyl ester, an oil. The more polar product, 1.767 g., was racemic trans-1-benzoyl-3-(2-chloroethyl)-4-piperidineacetic acid ethyl ester, an oil.

EXAMPLE 15

Preparation of rac. trans-1-benzoyl-3-(2-chloroethyl)-4-piperidineacetic acid from rac. trans-1-benzoyl-3-(2-chloroethyl)-4-piperidineacetic acid ethyl ester To a solution of 2.72 g. of racemic trans-1-benzoyl-3-(2-chloroethyl)-4-piperidineacetic acid ethyl ester in 37.5 ml. methanol, was added 37.5 ml. 1N sodium hydroxide solution. The mixture was stirred at room temperature for 36 hours. The methanol was removed by distillation. The residue was made acidic with 3N hydrochloric acid and extracted with methylene chloride. The extract was dried over anhydrous sodium sulfate, filtered, and evaporated to give 2.409 g. of crystalline racemic trans-1-benzoyl-3-(2-chloroethyl)-4-piperidineacetic acid, having a melting point of 122°–127° (from methylene chloride-ether).

EXAMPLE 16

Preparation of rac. trans-1-benzoyl-3-vinyl-4-piperidineacetic acid from rac. trans-1-benzoyl-3-(2-chloroethyl)-4-piperidineacetic acid To a solution of 5.71 g. of racemic trans-1-benzoyl-3-(2-chloroethyl)-4-piperidineacetic acid in 90 ml. anhydrous benzene was added 4.5 g. of potassium tert.-butoxide in 90 ml. dimethylsulfoxide. The mixture was stirred and heated at 70° under nitrogen overnight. The benzene was removed by distillation and after the addition of 75 ml. 1N sodium hydroxide solution, the residue was extracted with two 50 ml. portions of methylene chloride. The aqueous phase was made acidic with concentrated hydrochloric acid and extracted with three 500 ml. portions of benzene-ether 1:1 mixture. The extract was dried over anhydrous sodium sulfate, filtered and evaporated to give 4.9 g. of racemic trans-1-benzoyl-3-vinyl-4-piperidineacetic acid, which crystallized from ether on cooling, having a melting point of 138°–140°, and a melting point of 137°–141° after two recrystallizations from ether.

EXAMPLE 17

Preparation of rac. trans-1-benzoyl-3-vinyl-4-piperidineacetic acid methyl ester from rac. trans-1-benzoyl-3-vinyl-4-piperidineacetic acid To a stirred, ice-cold solution of 2.94 g. of racemic trans-1-benzoyl-3-vinyl-4-piperidineacetic acid in 45 ml. methanol, was added in two portions, a total of 68 ml. of diazomethane solution (~3 g./100 ml. in ethanol-ether). The stirring was continued for one hour. This was followed by the addition of several drops of glacial acetic acid and by evaporation to dryness. This gave 3.37 g. of crude product, which was chromatographed on 33 preparative silica gel plates with ethyl acetate and eluted with ethylacetate to yield 2.737 g. of racemic trans-1-benzoyl-3-vinyl-4-piperidineacetic acid methyl ester.

EXAMPLE 18

Preparation of trans-3-ethyl-4-piperidineacetic acid ethyl ester

A solution of 0.640 g. of trans-4-ethoxy-carbonyl-methyl-5-ethyl-2-piperidone and 0.684 g. of triethyloxonium fluoroborate in 20 ml. of anhydrous methylene chloride was stirred at room temperature for 65 hours, and then evaporated in vacuo. The resulting enol-ether was dissolved in 20 ml. of absolute ethanol, the solution was cooled to 0°C. and 0.25 g. of sodium borohydride was added in portions. The reaction mixture was stirred for 23 hours at room temperature, then diluted with 50 ml. of water and extracted with 1 l. of methylene chloride. Methylene chloride extract was washed with water (3 × 50 ml.), dried over anhydrous sodium sulfate and evaporated to dryness. The residue was dissolved in 7 ml. of ice-cold 1N hydrochloric acid. The resulting solution was diluted with 100 ml. of water, washed five times by shaking with 50 ml. of ether, and then made alkaline with 8 ml. of 1N sodium hydroxide and extracted with 1 l. of methylene chloride. The methylene chloride extract was washed three times with 50 ml. of water, dried over anhydrous sodium sulfate and evaporated to dryness to give 0.591 g. (99%) of trans-3-ethyl-4-piperidineacetic acid ethyl ester having a boiling point of 91°–92° (bath) at 0.5 mmHg.

Analysis Calcd. for $C_{11}H_{21}NO_2$ (199.29): C, 66.29; H, 10.62; N, 7.03; Found: C, 66.19; H, 10.79; N, 7.08.

EXAMPLE 19

Preparation of 3-[-benzoyl-3(R)-vinyl-4(R)-piperidine]propionic acid

A solution containing 10.9 g. of 3-[1-benzoyl-3(R)-(2-chloroethyl)-4(R)-piperidine]propionic acid ethyl ester in 150 ml. of methanol was combined with 150 ml. of 1N sodium hydroxide and allowed to stand at room temperature for 36 hours. The methanol was removed. The residue was rendered acidic by the addition of 3N hydrochloric acid and thereafter was extracted with dichloromethane. The combined organic layer was dried over sodium sulfate and evaporated under reduced pressure to give 10.2 g. of 3-[1-benzoyl-3(R)-(2-chloroethyl)-4(R)-piperidine]propionic acid. A solution of 10 g. of this material in 150 ml. of anhydrous benzene was added to a solution containing 7.5 g. of potassium-t-butoxide in 150 ml. of anhydrous dimethylsulfoxide. The mixture was stirred under an atmosphere of nitrogen overnight at 70°. After removal of benzene under reduced pressure, 125 ml. of 1N sodium hydroxide was added and the mixture was extracted with dichloromethane. The aqueous solution was acidified with concentrated hydrochloric acid and extracted with three portions of an ether-benzene mixture. The combined organic layers were washed with water, dried over sodium sulfate and evaporated under reduced pressure to give 6.9 g. (79 percent) of 3-[1-benzoyl-3(R)-vinyl-4(R)-piperidine]propionic acid. For analysis, a sample was recrystallized from ether, m.p. 132°–134°; $[\alpha]_D^{25}$ +64.31° (c 1.019, methanol).

EXAMPLE 20

Preparation of 3-[1-benzoyl-3(R)-vinyl-4(R)-piperidine]propionic acid ethyl ester A solution of 6.4 g. of 3-[1-benzoyl-3(R)-vinyl-4(R)-piperidine]propionic acid in 100 ml. of 4 percent ethanolic hydrogen chloride was left standing at room temperature for 15 hours. The solvent was removed under reduced pressure and the residue was again treated with 100 ml. of 4 percent ethanolic hydrogen chloride at room temperature overnight. After repeating this procedure once more, evaporation of the solvent under reduced pressure yielded 6.6 g. of 3-[1-benzoyl-3(R)-vinyl-4(R)-piperidine]propionic acid ethyl ester. Low boiling impurities were removed by distillation at 35° and a pressure of 0.1 mmHg. to give 5.9 g. of 3-[1-benzoyl-3(R)-vinyl-4(R)-piperidine]propionic acid ethyl ester, yield 79 percent.

We claim:

1. A process for the preparation of cis or trans 2-(1-acyl-3-vinyl-4-piperidine)acetic acids or esters, antipodes or racemates thereof or cis or trans 3-(1-acyl-3-vinyl-4-piperidine) propionic acids or esters or antipodes or racemates thereof which comprises the steps of:
   a. treating the corresponding cis or trans 2- or 3-(3-ethyl-4-piperidine)acetic or propionic acid or ester, antipode or racemate thereof with a chlorinating agent;
   b. irradiating the product of step (a), i.e., cis or trans 2- or 3-(1-chloro-3-ethyl-4-piperidine)acetic or propionic acid or ester, antipode or racemate thereof;
   c. treating the product of step (b), i.e., cis or trans 2- or 3-[3-(2-chloroethyl)-4-piperidine]acetic or propionic acid or ester, antipode or racemate thereof, with an acid chloride; and
   d. pyrrolyzing the product of step (c), i.e., cis or trans 2- or 3-[1-acyl-3-(2-chloroethyl)-4-piperidine]acetic or propionic acid or ester, antipode or racemate thereof, to yield the desired end product.

2. A process for the preparation of cis or trans 2-(1-acyl-3-vinyl-4-piperidine)acetic acid esters, antipodes or racemates thereof or cis or trans 3-(1-acyl-3-vinyl-4-piperidine) propionic acid esters or antipodes or racemates thereof which comprises the steps of:
   a. treating the corresponding cis or trans 2- or 3-(3-ethyl-4-piperidine)acetic or propionic acid ester, antipode or racemate thereof with a chlorinating agent;
   b. irradiating the product of step (a), i.e., cis or trans 2- or 3-(1-chloro-3-ethyl-4-piperidine)acetic or propionic acid ester, antipode or racemate thereof;
   c. treating the product of step (b), i.e., cis or trans 2- or 3-[3-(2-chloroethyl)-4-piperidine]acetic or propionic acid ester, antipode or racemate thereof, with an acid chloride; and
   d. pyrrolyzing the product of step (c), i.e., cis or trans 2- or 3-[1-acyl-3-(2-chloroethyl)-4-piperidine]acetic or propionic acid ester, antipode or racemate thereof, to yield the desired end product.

3. A process for preparing a compound of the formula

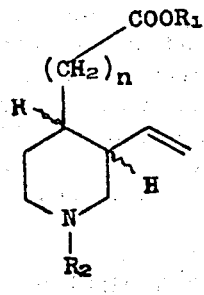

which comprises pyrrolyzing a compound of the formula

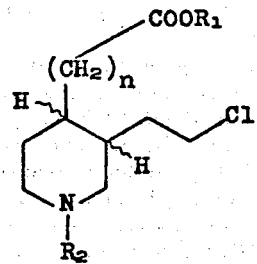

wherein $R_1$ is hydrogen or lower alkyl; $R_2$ is acyl, halo-substituted acyl, lower alkoxy-substituted acyl, lower alkyl-substituted acyl, and $n$ is 1 or 2.

* * * * *